United States Patent [19]
Frisk

[11] Patent Number: 5,928,607
[45] Date of Patent: Jul. 27, 1999

[54] BOTTLE STERILIZATION METHOD AND APPARATUS

[75] Inventor: Peter Frisk, Chicago, Ill.

[73] Assignee: Tetra Laval Holdings & Finance, SA, Pully, Switzerland

[21] Appl. No.: 08/911,970

[22] Filed: Aug. 15, 1997

[51] Int. Cl.$^6$ .............................. A61L 2/20; B65B 55/10
[52] U.S. Cl. ............................. 422/29; 422/24; 422/302; 53/425; 99/451; 426/392
[58] Field of Search ................................ 422/24, 29, 302; 53/425, 426; 426/407, 392, 521; 99/451, DIG. 14

[56] References Cited

U.S. PATENT DOCUMENTS

| | | |
|---|---|---|
| 1,984,457 | 12/1934 | Buttolph . |
| 2,546,205 | 3/1951 | Zimmerman . |
| 2,597,791 | 5/1952 | Graham-Enock . |
| 4,063,890 | 12/1977 | Baron . |
| 4,121,107 | 10/1978 | Bachmann . |
| 4,175,140 | 11/1979 | Bachmann et al. . |
| 4,289,728 | 9/1981 | Peel et al. . |
| 4,309,388 | 1/1982 | Tenney et al. ........................... 422/304 |
| 4,396,582 | 8/1983 | Kodera . |
| 4,944,132 | 7/1990 | Carlsson et al. . |
| 5,135,714 | 8/1992 | Wang . |
| 5,166,528 | 11/1992 | Le Vay . |
| 5,304,352 | 4/1994 | Bellettini et al. ....................... 422/186 |
| 5,326,542 | 7/1994 | Sizer et al. . |
| 5,334,355 | 8/1994 | Faddis ..................................... 422/122 |
| 5,433,920 | 7/1995 | Sizer et al. . |

*Primary Examiner*—E. Leigh McKane
*Attorney, Agent, or Firm*—Michael A. Catania

[57] ABSTRACT

The present invention discloses a method and an apparatus for sterilizing a container prior to filling the container with a pumpable food product such as milk, juice, water, soup or yogurt. The present invention uses UV radiation to transform oxygen into ozone at the filling station. The ozone flows into the container thereby sterilizing the container. Subsequently, the container is filled with a desired product and sealed. A preferred source of UV radiation is an excimer lamp.

17 Claims, 5 Drawing Sheets

BOTTLE STERILIZATION METHOD AND APPARATUS

BACKGROUND OF THE INVENTION

1. Field of the Invention

The present invention relates to a method and apparatus for sterilizing a bottle. Specifically, the present invention relates to a method and apparatus for sterilizing a bottle undergoing high speed aseptic filling through use of ozone.

2. Description of the Related Art

High speed aseptic bottle filling requires that the bottle be sterilized prior to the introduction of product. However, there is always the chance if the bottle is sterilized a sufficient time before filling that the bottle may become contaminated during the period between sterilization and filling. In order to alleviate this problem, the prior art has brought forth various solutions. One solution is to maintain a sterile environment throughout the transition period from sterilization to filling of the bottle. This solution would necessitate enclosing most of the filling machine within a sterile enclosure as well as the sterilized bottles. Other solutions may have the bottle sterilized downline from the filling station. Again, this necessitates an enclosure on the filling machine. What is needed is a way to provide a sterile bottle which diminishes the possibility of contamination without having to provide an entirely sterile environment for operation of the filling machine.

BRIEF SUMMARY OF THE INVENTION

The present invention provides a sterile container in a manner which almost entirely diminishes the possibility of contamination. The present invention is able to accomplish this by providing an apparatus which sterilizes the container just prior to filling.

One aspect of the present invention is an apparatus for sterilizing a container prior to aseptic filling of the container with a flowable material. The flowable material is usually maintained at a flowable material source, and the container has an opening with a predetermined diameter. The apparatus includes a fill pipe, an ultraviolet radiation source, a tube and a source of oxygen. The fill pipe delivers a desired contents such as juice, to the interior of the container. This delivery is accomplished in an aseptic manner with the fill pipe in flow communication with the interior of the container and the flowable material source.

The ultraviolet radiation source has a monochromatic wavelength less than 200 nanometers, and it encompasses the fill pipe near the opening of the container. The tube encompasses both the fill pipe and the ultraviolet radiation source, and provides a gap between the outer wall of the ultraviolet radiation source and the inner wall of the tube. The gap is in flow communication with the interior of the container. The tube has a filling end and a dispensing end. The source of oxygen is in flow communication with the gap and thereby in flow communication with the interior of the container. When oxygen flows from the source of oxygen through the gap passing by the ultraviolet radiation source it is transformed into ozone prior to ingress to the interior container where the ozone sterilizes the interior container prior to aseptic filling with the flowable material. The container may be from the group consisting of a PET bottle, a HDPE blow moulded bottle, a PET cup, a polyethylene bottle and a polypropylene bottle.

Another aspect of the present invention is an apparatus for aseptically sterilizing and filling bottles being conveyed along a filling and sealing machine at a single processing station on the machine. Each of the bottles has an opening of a predetermined diameter and are to be filled with a flowable material from a source of flowable material. The apparatus is as described above, and is integrated within the filling station of the multiple station machine.

Still another aspect of the present invention is a method for sterilizing bottles undergoing aseptic filling on a filling machine. The first step of the method is moving a bottle to be sterilized to a position near a processing station. The bottle must have an opening exposing the interior of the bottle. The next is providing an ultraviolet radiation source capable of generating a substantially monochromatic radiation less than 200 nanometers. The next step is flowing a predetermined quantity of oxygen gas pass the ultraviolet radiation source. The next step is irradiating the oxygen with sufficient radiation from the ultraviolet radiation source to convert the oxygen to ozone. The next step is flowing the ozone into the bottle thereby sterilizing the bottle. The final step is filling the sterilized bottle with a product.

It is a primary object of the present invention to provide a method for sterilizing a bottle just prior to filling the bottle with a desired product.

It is an additional object of the present invention to provide an apparatus for sterilizing a bottle, or a series of bottles just prior to filling with a desired product.

It is an additional object of the present invention to provide a bottled product that has an extended shelf life.

It is an additional object of the present invention to provide an apparatus integrated within the filling station of a filling and sealing machine, the apparatus sterilizing a bottle just prior to filling with a desired product.

It is yet a further object of the present invention to provide a method and apparatus for sterilizing a cup or a cap for a bottle.

Having briefly described this invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

Several features of the present invention are further described in connection with the accompanying drawings in which:

There is illustrated in FIG. 1 a schematic view of a preferred embodiment of the apparatus of the present invention.

Figure 1:
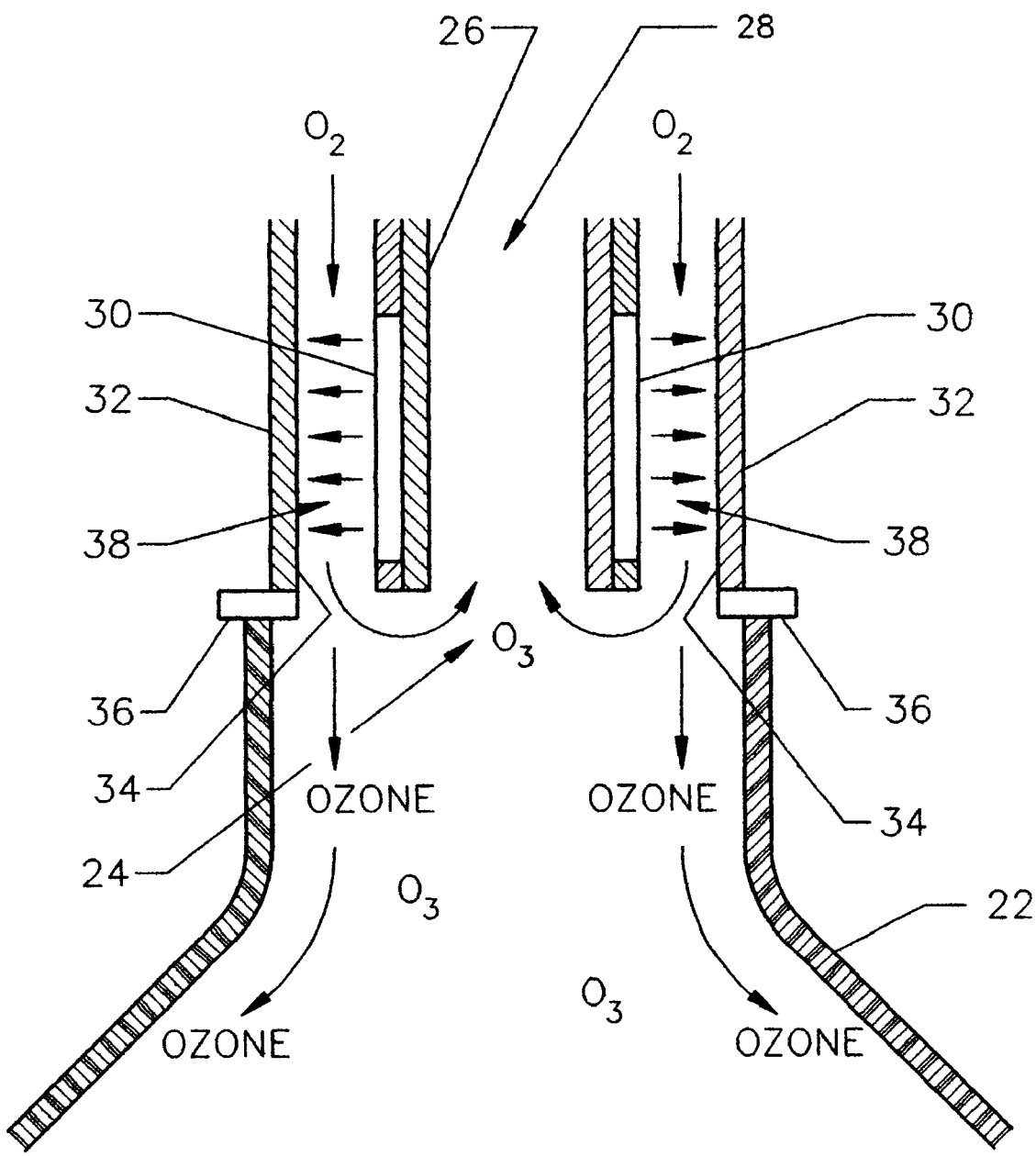
Figure 1A:
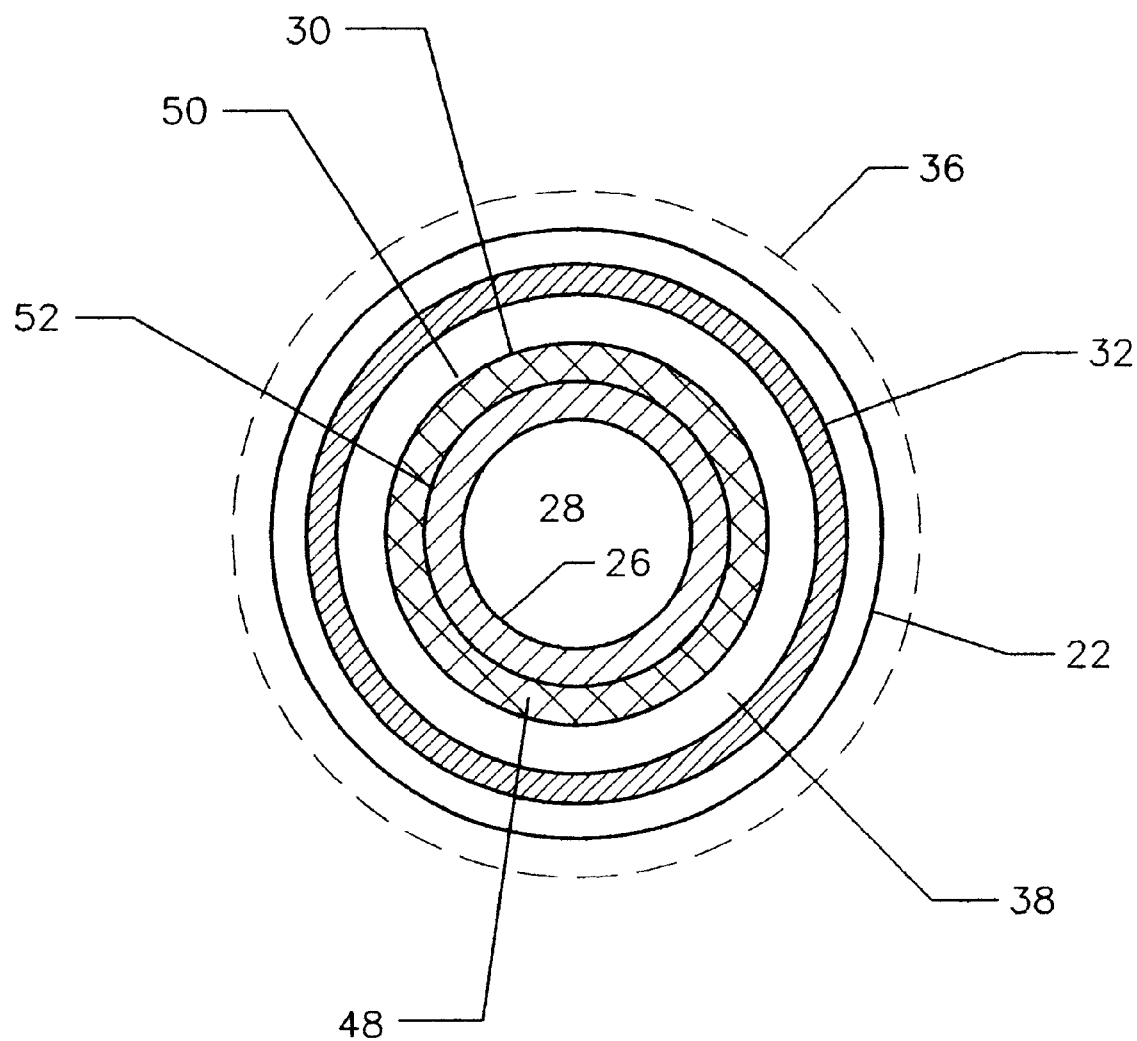

There is illustrated in FIG. 1A a cut-away view of the apparatus of the present invention.

Figure 2:
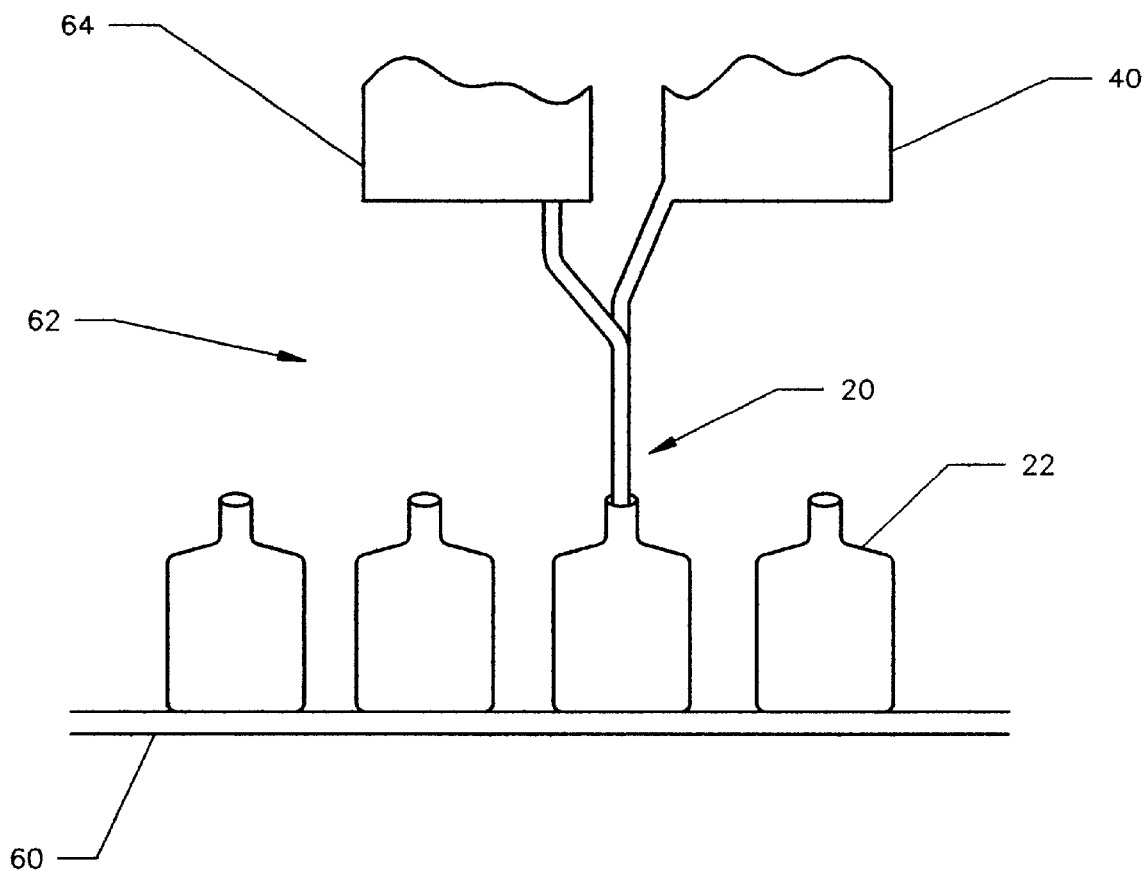

There is illustrated in FIG. 2 a schematic view of the apparatus of the present invention integrated on a filling station.

Figure 3:
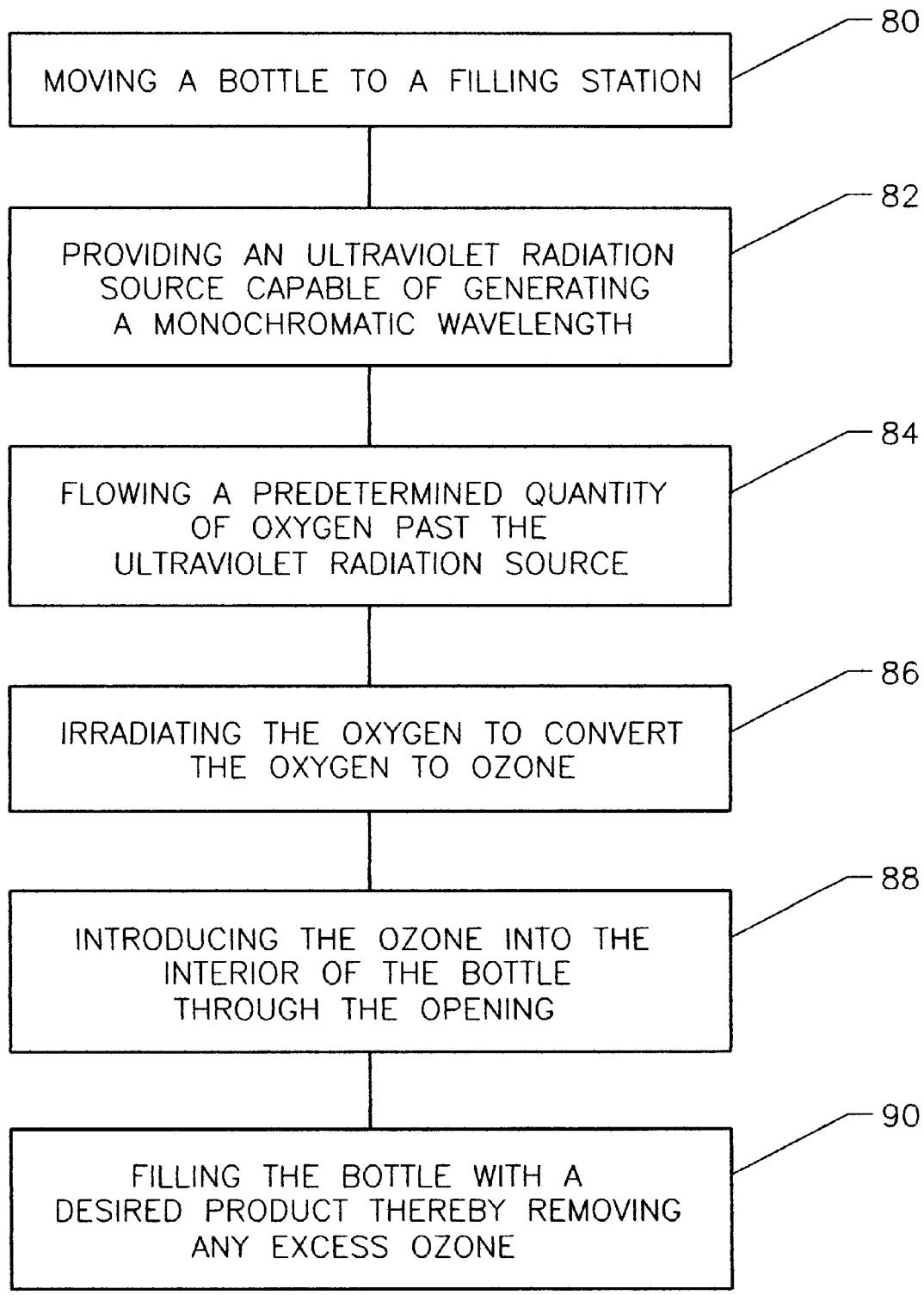

There is illustrated in FIG. 3 a flow diagram of the method of the present invention.

Figure 4:
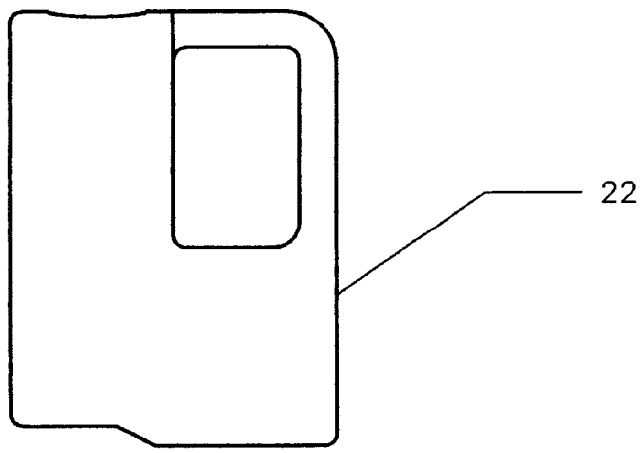

There is illustrated in FIG. 4 a blow moulded HDPE bottle sterilized using the present invention.

Figure 5:
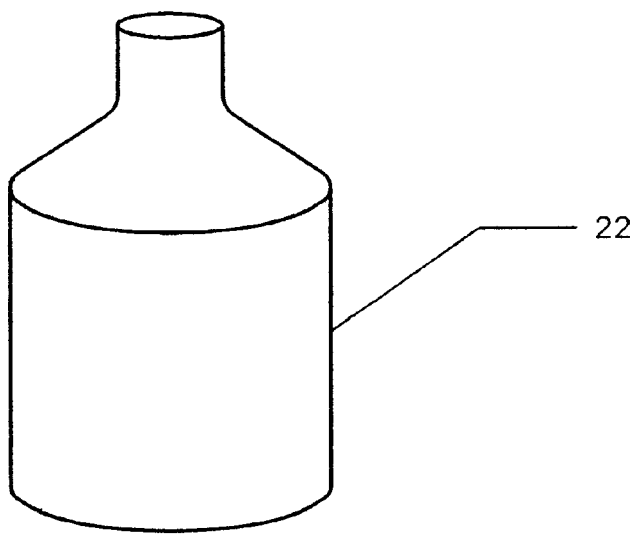

There is illustrated in FIG. 5 a PET bottle sterilized using the present invention.

DETAILED DESCRIPTION OF THE INVENTION

The present invention is to be used with a bottle filling and sealing machine. Any type of a bottle, cup, cap or container may be utilized, however, a polyethyleneterphthalate ("PET") bottle or a blow moulded high density polyethylene ("HDPE") are preferred. Other containers may be composed of polyethylene, polypropylene or copolymers thereof. The present invention sterilizes the bottle just prior to filling allowing for extended shelf life of the bottled product.

Oxygen/Ozone Transformation

Oxygen is vital to human survival whereas ozone is a gas which has quite deleterious effects on humans. Thus, it is interesting that one readily converts to the other and viz. versa. A possible mechanism is illustrated below:

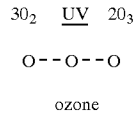

ozone

Ozone quickly degrades to oxygen, and thus the use of ozone as a sterilant must be able to overcome this rapid degradation between the generation of the ozone and the actual use of the ozone as a sterilant.

Excimer Ultraviolet Technology

The present invention may use excimer ultraviolet technology. Excimers are evanescent, electronically excited molecular complexes which exist only under unique conditions. The excimer is in an excited state as opposed to a ground state. In this excited state, elements such as the noble gases which are normally unreactive, are able to bind to one another or to other elements. Excimers usually disintegrate within a microsecond of formation and emit their binding energy as a photon as the two elements return to the ground state. For ultraviolet applications, the excimers formed from noble gas atoms or excimers formed from a noble gas and a halogen are of particular importance. Some of the more well known ultraviolet excimers include $Ar_2$, $Kr_2$, $Xe_2$, ArCl, KrCl, KrF and XeCl. These molecular complexes are ultraviolet excimers because the disintegration of the excimer, excited dimer, results in an emission in the ultraviolet range of the electromagnetic spectrum. For example, the emission from KrCl has a wavelength of 222 nanometers ("nm"), the emission from KrF has a wavelength of 248 nanometers, the emission from $Xe_2$ has a wavelength of 172 nm, and the emission from XeCl has a wavelength of 308 nm. Although several ultraviolet excimers have been mentioned in reference to the present invention, those skilled in the pertinent art will recognize that other ultraviolet excimers may be employed in practicing the present invention without departing from the scope of the present invention.

An example of the excimer process for xenon is as follows. First, a xenon atom in the ground state is excited by interaction with an electron to an excited state. Next, this excited xenon atom reacts with a ground state xenon atom to form an excimer complex. Within a microsecond after formation, the xenon atoms dissociate to two ground state xenon atoms and doing so emit an ultraviolet photon.

The present invention involves an excimer ultraviolet lamp in which a gas capable of forming excimers is hermetically sealed within a quartz glass shell. The gas may be a noble gas or a mixture of noble gas and a halogen. Electrons are generated by electrodes located outside of the shell and separated by a discharge gap. In a preferred embodiment, the excimer ultraviolet lamp is cylindrical in shape having an aperture therethrough the center. In this embodiment, one electrode is juxtaposed to the exterior surface of the ultraviolet lamp while the second electrode is juxtaposed on the interior surface of the cylinder of the ultraviolet lamp.

As shown in FIGS. 1 and 2, the apparatus 20 of the present invention is integrated within the filling station of the filling and sealing machine. More specifically, the apparatus modifies the fill pipe of a filling station. The apparatus 20 engages a bottle 22 thereby creating a flow communication between the opening 24, and thus the interior, of the bottle 22 and a fill pipe 26. The fill pipe 26 has a central aperture 28, which is the hallow interior of the fill pipe 26, from which the product flows into the bottle 22. Encompassing the fill pipe 26 near the opening 24 is the ultraviolet radiation source 30. Encompassing both the fill pipe 26 and the ultraviolet radiation source 30 is a tube 32 which has a diameter large enough to provide a gap 38 between the inner wall 34 of the tube 32 and the ultraviolet radiation source 30. In contact with the bottle 22 is a gasket 36 which may be composed of a FDA approved silicone rubber to maintain sterile environment and which is connected to the tube 32. The neck of the bottle 22 may be pressed against the gasket 36 to provide a tight seal to prevent the leakage of ozone. The compressive force may be provided by a lifter located under the bottle 22. Alternatively, a gripping mechanism attached to the tube 32 may be utilized to force the neck of the bottle 22 to the fill pipe 26.

Once a bottle 22 is connected to the apparatus 20, oxygen will flow through the gap 38 from a source 40, not shown. As the oxygen passes by the ultraviolet radiation source 30, the radiation converts the oxygen into ozone which flows into the bottle 22. The ozone sterilizes the bottle which is then immediately filled with a desired product which flows through the fill pipe 26. As the product flows into the bottle 22, the remaining ozone is evacuated/flushed from the bottle 22. Also, the ultraviolet radiation source 30 is cooled by the product. Once the bottle 22 is filled, it is conveyed to a sealing station. In this manner, the possibility of a bottle 22 becoming contaminated prior to filling is greatly reduced, if not entirely dismissed. The bottle 22 is actually still undergoing the sterilization process as the product is introduced into the bottle 22.

There is illustrated in FIG. 1A a top cross-section view of the apparatus of FIG. 1. As shown in FIG. 1 A, the various components of the apparatus 20 have a circular cross-section. However, those skilled in the art will recognize that other cross-sections such as an elliptical cross-section may be employed in practicing the present invention without departing from the spirit and scope of the present invention. The fill pipe 26 is encompassed by the ultraviolet radiation source 30. In a preferred embodiment, the ultraviolet radiation source 30 is an excimer lamp. The excimer ultraviolet lamp 30 may generally comprised of a cylindrical shell 48, an outer electrode 50 and an inner electrode 56. There is sealed within the cylindrical shell 48 a gas which is reacted to form excimers. The gas is electrically excited by an alternating voltage which causes a current flow in the discharge gap established between the inner electrode 52 and the outer electrode 50. The ultraviolet radiation generated by the excimers is generally directed outward from the cylindrical shell 48.

The excimer ultraviolet lamp 30 of the present invention operates at a significantly lower temperatures than traditional mercury based ultraviolet lamps. However, the excimer ultraviolet lamp 30 of the present invention still requires cooling to prevent overheating of the lamp 30, the fill pipe 26 and the bottle 22. To that end, the product flowing through the central aperture 28 of the fill pipe 26 into the bottle 22 acts to remove heat from the excimer ultraviolet lamp 30. the product may be maintained at a predetermined temperature which is below the operating temperature of the excimer ultraviolet lamp 30 in order for the cooling fluid to act as a heat sink to remove heat from the lamp 30 as the cooling fluid flows through the central aperture 28.

As shown in FIG. 2, a series of bottles 22 are conveyed along a conveyor system 60. At the filling station 62, the apparatus 20 connects to the bottle 22 thereby placing the fill pipe in flow communication with the interior of the bottle 22. The connection may be assisted by a vacuum created between the apparatus and the interior of the bottle 22, or through placement of the fill pipe 26 into the opening 24 of the bottle 22. Above the conveyor system 60 is a product tank 64 and a oxygen source 40. After each bottle 22 is sterilized and filled with a product, the bottle is conveyed to a sealing station further down the line.

A method of the present invention is set forth in the flow diagram of FIG. 3. At step 80, a bottle is moved toward the filling station of a filling and sealing machine. The bottle has an opening thereby exposing the interior of the bottle. The filling station as set forth in FIG. 1, has a fill pipe 26 for delivering a desired contents to the bottle 22. Surrounding the fill pipe 26 nearest the opening of the bottle 22 is a ultraviolet radiation source 30. Encompassing both the fill pipe 26 and the ultraviolet radiation source 30 is a tube 32 which has a diameter large enough to provide a gap 38 between the ultraviolet radiation source 30 and the inner wall 34 of the tube 32.

At step 82, an ultraviolet radiation source 30 capable of generating a substantially monochromatic radiation is provided. The radiation has a wavelength less than 200 nanometers. At step 84, a predetermined quantity of oxygen gas flows through the gap 38 and pass the ultraviolet radiation source 30. At step 86, the oxygen is irradiated with sufficient radiation from the ultraviolet radiation source 30 to convert the oxygen from oxygen to ozone. At step 88, the ozone is introduced to the interior of the bottle 22 thereby sterilizing the bottle 22. At step 90, the product is dispensed through the fill pipe 26 into the bottle 22 thereby evacuating the remaining ozone from the bottle 22 as the bottle 22 is filled with the product.

The desired product preferably may be milk, juice or water. However, other pumpable foods are within the scope of the present invention including soups, yogurts, cheeses, pastas and the like. The type of container, or the desired product should not be a limitation on the present invention as long as the container has an opening and the product is flowable.

There is shown in FIG. 4 a blow moulded HDPE bottle sterilized using the present invention. There is illustrated in FIG. 5 a PET bottle sterilized using the present invention.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes, modifications and substitutions of equivalents may be made therein without departing from the spirit and scope of this invention which is intended to be unlimited by the foregoing except as may appear in the following appended claims. Therefore, the embodiments of the invention in which an exclusive property or privilege is claimed are defined in the following appended claims:

I claim as my invention:

1. A method for sterilizing containers undergoing aseptic filling on a filling machine, the method comprising:

moving a container to be sterilized to a processing station, the container having an opening exposing the interior of the container, the processing station comprising
    a fill pipe for delivering a product to the interior of the container in an aseptic manner,
    an ultraviolet radiation source generating a monochromatic radiation having a wavelength less than 200 nanometers and encompassing the fill pipe at the opening of the container,
    a tube encompassing the fill pipe and the ultraviolet radiation source thereby providing a gap between an outer wall of the ultraviolet radiation source and an inner wall of the tube, the tube having a filling end and a dispensing end;

flowing a predetermined quantity of oxygen gas past the ultraviolet radiation source;

irradiating the oxygen with sufficient radiation from the ultraviolet radiation source to convert the oxygen to ozone;

flowing the ozone into the container thereby sterilizing the container; and filling the sterilized container with a product delivered through the fill pipe.

2. The method according to claim 1 further comprising the step of evacuating excess ozone from the container subsequent to the step of flowing the ozone into the container.

3. The method according to claim 1 wherein the container is selected from the group consisting of a PET bottle, a HDPE blow moulded bottle, a PET cup, a polyethylene bottle and a polypropylene bottle.

4. The method according to claim 1 wherein the ultraviolet radiation source is an excimer ultraviolet lamp having a monochromatic wavelength.

5. The method according to claim 4 wherein the excimer ultraviolet lamp comprises a shell filled with xenon gas.

6. The method according to claim 1 wherein the gap is an annular gap.

7. The method according to claim 1 wherein the tube has a diameter smaller than that of the diameter of the opening of the container.

8. The method according to claim 1 wherein the product cools the ultraviolet radiation source as the product flows into the interior of the container.

9. An apparatus for sterilizing a container prior to aseptic filling of the container with a flowable material, the flowable material maintained at a flowable material source, the container having an opening with a predetermined diameter, the apparatus comprising:

a fill pipe for delivering a flowable material to an interior of the container in an aseptic manner, the fill pipe in flow communication with the interior of the container and the flowable material source;

an ultraviolet radiation source having a monochromatic wavelength less than 200 nanometers, the ultraviolet radiation source encompassing the fill pipe at the opening of the container;

a tube encompassing the fill pipe and the ultraviolet radiation source thereby providing a gap between an outer wall of the ultraviolet radiation source and an inner wall of the tube, the gap in flow communication with the interior of the container, the tube having an filling end and a dispensing end; and a source of oxygen in flow communication with the gap and thereby in flow communication with the interior of the container;

whereby oxygen flows from the source of oxygen through the gap passing by the ultraviolet radiation source thereby becoming ozone prior to ingress to the interior container where the ozone sterilizes the interior container prior to aseptic filling with the flowable material.

10. The apparatus according to claim 9 wherein the ultraviolet radiation source is an excimer ultraviolet lamp having a monochromatic wavelength.

11. The apparatus according to claim 10 wherein the excimer ultraviolet lamp comprises a shell filled with xenon gas.

12. The apparatus according to claim 9 wherein the gap is an annular gap.

13. The apparatus according to claim 9 wherein the tube has a diameter smaller than that of the diameter of the opening of the container.

14. The apparatus according to claim 9 wherein the flowable material cools the ultraviolet radiation source as the flowable material flows into the interior of the container.

15. The apparatus according to claim 9 further comprising a gasket connected to the open end of the tube, the gasket contacting the container and providing a temporary seal between the tube and the container.

16. The apparatus according to claim 15 wherein the gasket is a flexible silicone membrane resistant to ozone.

17. The apparatus according to claim 9 wherein the tube is composed of a stainless steel material.

* * * * *